(12) United States Patent
Yoon et al.

(10) Patent No.: US 9,931,411 B2
(45) Date of Patent: Apr. 3, 2018

(54) MICROPARTICLES CONTAINING PHYSIOLOGICALLY ACTIVE PEPTIDE, METHOD FOR PREPARING THE SAME, AND PHARMACEUTICAL COMPOSITION COMPRISING THE SAME

(71) Applicant: SAMYANG BIOPHARMACEUTICALS CORPORATION, Seoul (KR)

(72) Inventors: Hye Jeong Yoon, Daejeon (KR); Min Hyo Seo, Daejeon (KR); Yil Woong Yi, Daejeon (KR); Bong Oh Kim, Daejeon (KR)

(73) Assignee: SAMYANG BIOPHARMACEUTICALS CORPORATION, Seoul (KR)

( * ) Notice: Subject to any disclaimer, the term of this patent is extended or adjusted under 35 U.S.C. 154(b) by 0 days.

(21) Appl. No.: 15/065,261

(22) Filed: Mar. 9, 2016

(65) Prior Publication Data

US 2016/0184444 A1 Jun. 30, 2016

Related U.S. Application Data

(62) Division of application No. 13/996,917, filed as application No. PCT/KR2011/010004 on Dec. 22, 2011, now abandoned.

(30) Foreign Application Priority Data

Dec. 24, 2010 (KR) ........................ 10-2010-0134223

(51) Int. Cl.
| | | |
|---|---|---|
| *A61K 47/48* | (2006.01) | |
| *A61K 38/08* | (2006.01) | |
| *A61K 9/00* | (2006.01) | |
| *A61K 9/16* | (2006.01) | |
| *A61J 3/02* | (2006.01) | |
| *A61K 9/14* | (2006.01) | |
| *A61K 38/22* | (2006.01) | |
| *A61K 47/59* | (2017.01) | |
| *A61K 47/69* | (2017.01) | |
| *A61K 38/00* | (2006.01) | |

(52) U.S. Cl.
CPC .............. *A61K 47/482* (2013.01); *A61J 3/02* (2013.01); *A61K 9/0019* (2013.01); *A61K 9/146* (2013.01); *A61K 9/1647* (2013.01); *A61K 38/08* (2013.01); *A61K 38/22* (2013.01); *A61K 47/593* (2017.08); *A61K 47/6927* (2017.08); *A61K 38/00* (2013.01)

(58) Field of Classification Search
CPC . A61K 38/08; A61K 47/482; A61K 47/48876
See application file for complete search history.

(56) References Cited

U.S. PATENT DOCUMENTS

| | | | |
|---|---|---|---|
| 4,673,595 A | 6/1987 | Orsolini et al. | |
| 5,134,122 A | 7/1992 | Orsolini | |
| 5,271,945 A | 12/1993 | Yoshioka et al. | |
| 5,366,734 A | 11/1994 | Hutchinson | |
| 6,221,958 B1 * | 4/2001 | Shalaby | A61K 47/482 514/10.3 |
| 6,506,410 B1 | 1/2003 | Park et al. | |
| 6,630,156 B1 | 10/2003 | Seo et al. | |
| 2003/0026844 A1 | 2/2003 | Lee et al. | |
| 2007/0275082 A1 | 11/2007 | Lee et al. | |
| 2008/0292714 A1 * | 11/2008 | Garlich | A61K 9/5153 424/501 |
| 2009/0136583 A1 | 5/2009 | Park et al. | |
| 2011/0177139 A1 | 7/2011 | Jung et al. | |

FOREIGN PATENT DOCUMENTS

| | | | |
|---|---|---|---|
| CN | 101721370 A | 6/2010 | |
| EP | 0190833 A2 | 8/1986 | |
| EP | 0535937 A1 | 4/1993 | |
| EP | 0601799 A1 | 6/1994 | |
| JP | 4-36233 A | 2/1992 | |
| JP | 9-509161 A | 9/1997 | |
| KR | 10-2010-0075955 A | 7/2010 | |
| WO | WO 95/22318 A1 | 8/1995 | |
| WO | WO2005/107813 * | 11/2005 | ............. A61K 47/54 |
| WO | WO 2005/107813 A1 | 11/2005 | |
| WO | WO 2006/123361 A2 | 11/2006 | |
| WO | WO 2008/136611 A1 | 11/2008 | |
| WO | WO 2009/042231 * | 4/2009 | ............... A61K 9/16 |
| WO | WO 2009/042231 A2 | 4/2009 | |
| WO | WO 2010/039007 A2 | 4/2010 | |

OTHER PUBLICATIONS

Xu et al. (Small. Jul. 2009; 5 (13): 1575-1581.*
Freitas, et al. (Journal of Controlled Release 102 (2005) 313-332).*
Acharya et al., "The Hydrogel Template Method for Fabrication of Homogeneous Nano/Microparticles", Journal of Controlled Release, vol. 141, 2010, pp. 314-319.
Kondo, "Microcapsules—Applications and Functions," First edition, Japanese Standard Association, Mar. 20, 1991, pp. 78-79, with concise English explanation of relevance.
Kondo, "Microcapsules," Industrial Technology Library—25, First edition, Japanese Standard Association, Apr. 20, 1975, pp. 100-101, with concise English explanation of relevance.
Ye et al., "Issues in long-term protein delivery using biodegradable microparticles", Journal of Controlled Release, vol. 146, 2010, (Available online May 19, 2010), pp. 241-260.

(Continued)

*Primary Examiner* — Anna Falkowitz

(74) *Attorney, Agent, or Firm* — Birch, Stewart, Kolasch & Birch, LLP

(57) ABSTRACT

Disclosed are microparticles containing physiologically active peptides, a method for preparing the same, and a pharmaceutical composition comprising the same.

13 Claims, 2 Drawing Sheets

(56) References Cited

OTHER PUBLICATIONS

International Search Report for Appl. No. PCT/KR2011/010004 dated Jun. 21, 2012.

* cited by examiner

MICROPARTICLES CONTAINING PHYSIOLOGICALLY ACTIVE PEPTIDE, METHOD FOR PREPARING THE SAME, AND PHARMACEUTICAL COMPOSITION COMPRISING THE SAME

This application is a Divisional of U.S. patent application Ser. No. 13/996,917 filed on Jun. 21, 2013, which is the national stage entry of international application PCT/KR2011/010004 filed on Dec. 22, 2011, which claims priority to Application No. 10-2010-0134223 filed in Korea on Dec. 24, 2010, all of which are hereby expressly incorporated by reference into the present application.

BACKGROUND OF THE INVENTION

Field of the Invention

The present invention relates to microparticles containing physiologically active peptides, a method for preparing the same, and a pharmaceutical composition comprising the same. More specifically, the present invention relates to microparticles which comprise an ionic complex of physiologically active peptide and water-soluble polymer, and a biodegradable water-insoluble polymer, and thus can reduce initial burst of peptide drugs and control the release rate, by which the therapeutic effects of drugs can be improved; a method for preparing the same; and a pharmaceutical composition comprising the same for peptide drugs.

Description of the Related Art

Conventional formulations for injection such as infusion solutions, suspensions and emulsions are rapidly removed from the body after they are intramuscularly or subcutaneously administered. For this reason, frequent administration by injection is required for treatment of chronic diseases. In an attempt to solve this problem, microencapsulation—a process in which a drug is encapsulated into microspheres—has been suggested. Microspheres are produced in a size of unit of several μm to several tens of and thus can be injected intramuscularly or subcutaneously. Accordingly, they can control the drug release rate and thus can adjust the drug delivery period. Therefore, a therapeutically effective drug concentration can be maintained for a long period of time by a single administration.

Generally, after oral administration, most peptide drugs lose their active structures or are broken down by enzymatic degradation under acidic environments, and are poorly absorbed in the gastric or intestinal mucosa. For this reason, peptide drugs are administered by injection. Peptide drugs should be injected continuously and repeatedly because of their short half-life and low bioavailability in vivo. It is also frequently required to administer peptide drugs for a long period of several months. Accordingly, a great deal of research on sustained and controlled release formulations using biodegradable polymers is actively underway.

Aliphatic polyesters have been developed and their bioavailability has been approved by the U.S. Food and Drug Administration (U. S. FDA), and they are currently used as polymeric carriers for peptide drugs. Aliphatic polyesters are widely utilized in applications including carriers for drug delivery, surgical sutures and the like.

Recently, physiologically active peptides have been developed as novel drugs and thus a variety of approaches to continuously release the drugs by encapsulating these drugs in polymer carriers has been conducted. However, such formulations where peptide drugs are encapsulated in microspheres comprising an aliphatic polyester, have disadvantages including initial burst (excessive release) effect of drugs, difficulty in maintaining the drug release rate constantly for a predetermined period of time, and incomplete release, i.e., the release of less than 100% of the encapsulated drug. The initial burst of drug is due to the fact that peptide drugs adsorbed on the surface and pores of microspheres are rapidly diffused and released at an initial stage. Accordingly, there is a demand for a method for preparing sustained-release microspheres containing peptide, by which the initial burst of drugs is avoided and 100% of the encapsulated drug is released at a zero-order rate during the release period of time. It is also required that the method is simple, the encapsulation ratio of the drug is high, the encapsulated drug is highly stable and the method is economically efficient.

It has been known that the methods for preparing drug-containing microspheres include phase separation, melt-extrusion, followed by cryopulverization, double emulsion evaporation (W/O/W, water/oil/water), single emulsion evaporation (O/W, oil/water), spray drying and the like.

The phase separation disclosed in U.S. Pat. No. 4,673,595 is a method for preparing microparticles by dissolving a polymer in methylene chloride. This method uses methylene chloride in combination with silicone oil, ethyl alcohol, etc., and thus has a disadvantage of the complicated overall process to remove all of the used organic solvents.

U.S. Pat. No. 5,134,122 discloses the melt extrusion followed by cryopulverization. This method is free from the risk of residual toxic solvents since no toxic solvent is used in the preparation process. However, peptides may be denatured due to the heat generated during the grinding procedures to obtain PLGA microparticles and peptide microparticles. It is also difficult to control the size of the obtained microparticles to a level suitable for easy injection.

The emulsion evaporation (W/O/W) is generally used. U.S. Pat. No. 5,271,945 discloses a method in which an aqueous solution containing a peptide is dispersed in an organic solvent containing a biodegradable polymer to form a primary emulsion (W/O) and the primary emulsion is then dispersed in an aqueous phase containing an emulsifying agent. However, when microparticles are prepared by such emulsion evaporation, the microparticles may exhibit different biological response levels due to the wide range of particle size distribution and thus it is difficult to predict pharmaceutical effects. Furthermore, it is difficult to develop clinically useful carriers due to the existence of the particles much bigger than the average size.

In addition, since most bio-peptide drugs are water-soluble, said methods have disadvantages in that a considerable amount of drugs escapes in the aqueous phase during the dispersing process and thus the encapsulation ratio becomes low.

SUMMARY OF THE INVENTION

Therefore, the present invention has been made in view of the above problems, and it is an object of the present invention to provide polymeric microparticles containing physiologically active peptides and a biodegradable, water-insoluble polymer; and a method for conveniently preparing the same. The microparticles of the present invention have a uniform size, efficiently encapsulate physiologically active peptides therein, reduce the initial burst of drug and exhibit the sustained release for a predetermined period. In addition, the present method for preparing the microparticles does not use an organic solvent excessively, and the residual minor amount of the organic solvent can be removed efficiently, and thus any toxicity caused by organic solvents can be prevented. Also, the preparation can be conducted in a simple manner.

In accordance with one aspect of the present invention, the above and other objects can be accomplished by the provision of a microparticle comprising an ionic complex of physiologically active peptide and water-soluble polymer, and a biodegradable, water-insoluble polymer.

In accordance with another aspect of the present invention, provided is a method for preparing physiologically active peptide-containing polymer complex comprising: 1) mixing a physiologically active peptide with an ionic water-soluble polymer in an aqueous medium to form an ionic complex of the physiologically active peptide and the water-soluble polymer; and 2) drying the ionic complex of the physiologically active peptide and the water-soluble polymer obtained in step 1).

In accordance with another aspect of the present invention, provided is a method for preparing physiologically active peptide-containing microparticle comprising: a) homogeneously mixing an ionic complex of a physiologically active peptide and a water-soluble polymer with a biodegradable, water-insoluble polymer in a non-aqueous solvent; and b) removing the non-aqueous solvent from the resulting solution obtained in step a) to obtain microparticle.

In accordance with yet another aspect of the present invention, provided is a pharmaceutical composition comprising the microparticle containing physiologically active peptide according to the present invention, and a pharmaceutically acceptable carrier.

Effect of the Invention

The microparticle containing physiologically active peptide according to the present invention exhibits high encapsulation efficiency of peptide drug, is of no initial burst of the peptide drug and can continuously release the drug for a long period of time. In addition, since the microparticles are prepared in a relatively uniform size, the deviation between production batches decreases and thus the microparticles can be prepared with a uniform quality.

DETAILED DESCRIPTION OF THE INVENTION

Figure 1:
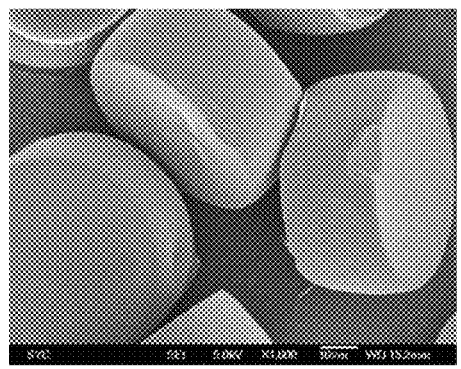
FIG. 1 is a scanning electronic microscope (SEM) image showing the microparticles prepared in Example 9 of the present invention.

Hereinafter, the present invention will be described in detail.
<Physiologically Active Peptide>
As the physiologically active peptide contained in microparticles of the present invention, any water-soluble physiologically active peptide known as a drug and a pharmaceutically acceptable salt thereof may be used without particular limitation. Examples of the physiologically active peptide include, but are not limited to, LHRH analogs such as LHRH agonists or LHRH antagonists, somatostatin and analogs thereof, glucagon-like peptides (GLP), parathyroid hormone and analogs thereof, insulin-like growth factors, epidermal growth factors, platelet-derived growth factors, fibroblast growth factors, transforming growth factors, growth hormone releasing factors, amylin analogs, peptide YY (PYY), protein synthesis-stimulating peptides, gastrin inhibitory peptides, vasoactive intestinal peptides and pharmaceutically acceptable salts thereof.

Examples of the LHRH agonists include goserelin, leurporeline, triptorelin, buserelin, nafarelin, fertirelin, deslorelin, gonandorelin, alarelin, antide and the like, and examples of the LHRH antagonists include cetrorelix, argitide, orntide and the like.

Examples of the glucagon-like peptides (GLP) include GLP-1, exenatide, liraglutide, taspoglutide, albiglutide, lixisenatide and the like.

Examples of somatostatin and analogs thereof include somatostatin, octreotide, lanreotide, vapreotide and the like.

Examples of vasopressin and analogs thereof include lypressin, oxytocin, argipressin, desmopressin and the like.

Other examples include calcitonin, elcatonin, corticotropin releasing factors, brain natriuretic peptides, thymosin, thymopentin, corticotropin, beta-amyloid, angiotensin, atosiban, bivalirudin, cetrorelix, enfuvirtide, nesiritide, eptifibatide, secretin, teriparatide, terlipressin, tetracosactide, pramlintide and the like.

In the microparticles of the present invention, the physiologically active peptide is preferably present in an amount of 1.0 to 10% by weight, more preferably, 2.0 to 5.0% by weight, with respect to the total weight of the microparticles. When the peptide is present in an amount less than 1.0% by weight with respect to the total weight of the microparticles, the amount of microparticles to be administered to a patient increases excessively and thus the administration may be problematic or impossible. When the peptide is present in an amount greater than 10% by weight, the inhibition of initial burst may be difficult.
<Ionic Water-Soluble Polymer>
In the present invention, an ionic water-soluble polymer is used for formation of an ionic complex with the aforesaid physiologically active peptide. The ionic water-soluble polymer used in the present invention is a water-soluble polymer which is ionized in an aqueous solution and then takes positive or negative charge. It may form a complex having ionic bond with anion or cation of charged amino acid in the physiologically active peptide.

The ionic water-soluble polymer is not particularly limited, and examples thereof include, for example, polylactic acid having at least one terminal carboxyl group or a derivative thereof. According to an embodiment of the present invention, the polylactic acid having at least one terminal carboxyl group or a derivative thereof is one or more selected from the group consisting of polylactic acid, polylactide, polyglycolide, polymandelic acid, polycaprolactone, polyanhydride and copolymers thereof.

The remaining terminal group(s) other than the terminal carboxyl group(s) of the polylactic acid or a derivative thereof is one or more terminal groups selected from the group consisting of hydroxy, acetoxy, benzoyloxy, decanoyloxy, palmitoyloxy, methyl and ethyl. Since the polylactic acid or a derivative thereof has anionic terminal carboxyl group(s), it may form an ionic complex with the cationic amine group of amino acid of the physiologically active peptide.

The number average molecular weight of the polylactic acid or a derivative thereof is preferably 500 to 5,000 daltons, more preferably 1,000 to 3,000 daltons, and most preferably 1,000 to 2,000 daltons. When the molecular weight is lower than 500 daltons, water-insolublity of the ionic complex with the physiologically active peptide may be insufficient. When the molecular weight is higher than 5,000 daltons, the polylactic acid or a derivative thereof is not dissolved in water and thus it may be difficult to form the ionic complex. Accordingly, the above range is preferred.

In the present invention, the polylactic acid having at least one terminal carboxyl group or a derivative thereof is preferably one or more selected from the group consisting of compounds represented by Formulae 1 to 6 below:

$$RO-CHZ-[A]_n-[B]_m-COOM \quad \text{[Formula 1]}$$

wherein A is —COO—CHZ—; B is —COO—CHY—, —COO—$CH_2CH_2CH_2CH_2CH_2$— or —COO—$CH_2CH_2OCH_2$; R is hydrogen atom, or acetyl group, benzoyl group, decanoyl group, palmitoyl group, methyl group or ethyl group; each of Z and Y independently is hydrogen atom, methyl group or phenyl group; M is H, Na, K, or Li; n is an integer of 1 to 30; and m is an integer of 0 to 20, $$RO-CHZ-[COO-CHX]_p-[COO-CHY']_q-COO-CHZ-COOM \quad \text{[Formula 2]}$$

wherein X is methyl group; Y' is hydrogen atom or phenyl group; p is an integer of 0 to 25 and q is an integer of 0 to 25 provided that p+q is an integer of 5 to 25; R is hydrogen atom, or acetyl group, benzoyl group, decanoyl group, palmitoyl group, methyl group or ethyl group; M is H, Na, K, or Li; and Z is hydrogen atom, methyl group or phenyl group, $$RO-PAD-COO-W-M' \quad \text{[Formula 3]}$$

wherein W-M' is

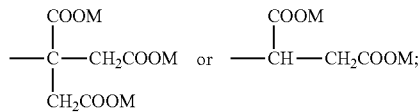

PAD is selected from the group consisting of D,L-polylactic acid, D-polylactic acid, polymandelic acid, copolymer of D,L-lactic acid and glycolic acid, copolymer of D,L-lactic acid and mandelic acid, copolymer of D,L-lactic acid and caprolactone, and copolymer of D,L-lactic acid and 1,4-dioxan-2-one; R is hydrogen atom, acetyl group, benzoyl group, decanoyl group, palmitoyl group, methyl group or ethyl group; and M is independently H, Na, K, or Li, $$S-O-PAD-COO-Q \quad \text{[Formula 4]}$$

wherein S is

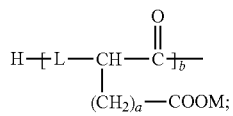

L is —$NR_1$— or —O— in which $R_1$ is hydrogen atom or $C_{1-10}$ alkyl; Q is $CH_3$, $CH_2CH_3$, $CH_2CH_2CH_3$, $CH_2CH_2CH_2CH_3$, or $CH_2C_6H_5$; a is an integer of 0 to 4; b is an integer of 1 to 10; M is H, Na, K, or Li; PAD is one or more selected from the group consisting of D,L-polylactic acid, D-polylactic acid, polymandelic acid, copolymer of D,L-lactic acid and glycolic acid, copolymer of D,L-lactic acid and mandelic acid, copolymer of D,L-lactic acid and caprolactone, and copolymer of D,L-lactic acid and 1,4-dioxan-2-one,

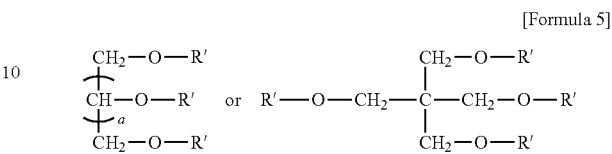

[Formula 5]

wherein R' is —PAD-O—C(O)—$CH_2CH_2$—C(O)—OM, in which PAD is selected from the group consisting of D,L-polylactic acid, D-polylactic acid, polymandelic acid, copolymer of D,L-lactic acid and glycolic acid, copolymer of D,L-lactic acid and mandelic acid, copolymer of D,L-lactic acid and caprolactone, and copolymer of D,L-lactic acid and 1,4-dioxan-2-one, and M is H, Na, K, or Li; and a is an integer of 1 to 4, for example, 3-arm PLA-COONa provided a=1; 4-arm PLA-COONa provided a=2; 5-arm PLA-COONa provided a=3, and 6-arm PLA-COONa provided a=4, $$YO-[-C(O)-(CHX)_a-O-]_m-C(O)-R-C(O)-[-O-(CHX')_b-C(O)-]_n-OZ \quad \text{[Formula 6]}$$

wherein each of X and X' is independently hydrogen, alkyl (for example, alkyl having 1 to 10 carbon atoms such as methyl) or aryl (for example, aryl having 6 to 20 carbon atoms such as phenyl); each of Y and Z is independently H, Na, K, or Li; each of m and n is independently an integer of 0 to 95 provided that 5<m+n<100; each of a and b is each independently an integer of 1 to 6; and R is substituted or unsubstituted —$(CH_2)_k$— in which k is an integer of 0 to 10, divalent alkenyl having 2 to 10 carbon atoms, divalent aryl having 6 to 20 carbon atoms, or a combination thereof.

In the present invention, the used amount of the ionic water-soluble polymer (for example, polylactic acid having at least one terminal carboxyl group or a derivative thereof) is specifically from 0.1 to 10 times of moles, more specifically 0.5 to 5 times of moles, and even more specifically 1 to 2 times of moles, with respect to the used amount of the physiologically active peptide. When the used amount of the ionic water-soluble polymer is less than 1 time of moles with respect to the used amount of the physiologically active peptide, there may be a peptide incapable of forming the ionic complex. When the used amount of the ionic water-soluble polymer is greater than 10 times of moles with respect to the used amount of the physiologically active peptide, the prepared microparticles may be readily dissolved and released during a subsequent washing process and thus porosity of particles disadvantageously increases and, as a result, the release rate may decrease. In addition, the ionic polymer present in the microparticle may be decomposed to generate a considerable amount of acid that makes the microenvironment in the microparticle acidic, which may then increase the degradation rate of other polymers present in the microparticle and accordingly the peptide may be exposed to unstable environment.

<Ionic Complex of the Physiologically Active Peptide and the Water-Soluble Polymer>

In the present invention, the physiologically active peptide and the ionic water-soluble polymer as described above form a complex through ionic bonding. For example, biodegradable polymeric polylactic acid having at least one terminal carboxyl group or a derivative thereof is readily ionized in water and takes negative charge, and thus forms an ionic bond with positively charged amino acid that constitutes the physiologically active peptide. When the microparticles are prepared by using the ionic complex prepared as such, peptide loss may be reduced, the encapsulation ratio of peptide can be improved and the initial burst can be reduced. The complexes are present in the present microparticle as a distributed form therein.

Thus, in accordance with another aspect of the present invention, provided is a method for preparing physiologically active peptide-containing polymer complex comprising: 1) mixing a physiologically active peptide with an ionic water-soluble polymer in an aqueous medium to form an ionic complex of the physiologically active peptide and the water-soluble polymer; and 2) drying the ionic complex of the physiologically active peptide and the water-soluble polymer obtained in step 1).

In the preparation method of the physiologically active peptide-containing polymer complex, the physiologically active peptide and ionic water-soluble polymer used may be the same as those described above.

In step 1), the physiologically active peptide and the ionic water-soluble polymer may be independently dissolved in separate aqueous media such as water to prepare respective aqueous solutions thereof and these aqueous solutions may then be mixed. Alternatively, the physiologically active peptide and ionic water-soluble polymer are simultaneously added to an aqueous medium and mixed to prepare the complex. When the aqueous solution of the physiologically active peptide is separately prepared and used, pH of the aqueous solution is preferably 4.0 to 10.0, more preferably pH is 4.5 to 7.5, and even more preferably pH is 5.5 to 6.5.

In one embodiment of the present invention, when an alkali metal salt of polylactic acid having at least one terminal carboxyl group or a derivative thereof is used as the ionic water-soluble polymer, the alkali metal salt has a compound form in which the terminal carboxyl group of the polylactic acid or a derivative thereof is ionically bonded to an alkali metal. Concretely, such a compound form may be obtained by neutralizing the polylactic acid having a terminal carboxyl group or a derivative thereof with sodium, potassium, lithium or the like. In this case, the alkali metal may be provided from sodium carbonate, sodium hydrogen carbonate, potassium carbonate, potassium hydrogen carbonate, potassium carbonate or the like.

The mixing ratio of the physiologically active peptide:the ionic water-soluble polymer (for example, polylactic acid having at least one terminal carboxyl group or a derivative thereof) is specifically 1:0.5 to 10, more specifically 1:0.5 to 5, and even more specifically 1:1 to 2 as a molar ratio. Problems which may occur when the mixing ratio is beyond this range are described above.

In step 2), the drying may be carried out by a method such as freeze-drying, vacuum drying or the like.

<Biodegradable, Water-Insoluble Polymer>

The biodegradable, water-insoluble polymer contained in the microparticle of the present invention is a conventional polymer used for preparation of microparticles and a biodegradable aliphatic polyester, which is insoluble in water but is hydrolyzed in vivo, is generally used. Such a biodegradable, water-insoluble polymer serves as a matrix containing the ionic complex of the physiologically active peptide and water-soluble polymer as described above.

Specific examples of the biodegradable, water-insoluble polymers useful for the present invention include polylactide (PLA), polyglycolide (PGA), poly(lactide-co-glycolide) (PLGA) which is a copolymer thereof, polyorthoester, polycaprolactone, polydioxanone, polyalkylcarbonate, polyanhydride and copolymers thereof. Polylactide, polyglycolide and poly(lactide-co-glycolide) which is a copolymer thereof are preferred. The biodegradable, water-insoluble polymers (in particular, polyesters such as PLA, PGA and PLGA) are biocompatible and stable substances since they are hydrolyzed in vivo and are converted into nontoxic lactic acid or glycolic acid. Their biodegradation rate can also be controlled to one to two weeks at minimum and one to two years at maximum, depending on the molecular weight of polymers, ratio of monomers and hydrophilicity. Thus they are suitable for use in the present invention. One embodiment of the present invention uses poly(lactide-co-glycolide) in which the content of lactide is from 50% by weight to 85% by weight and the content of glycolide is from 15% by weight to 50% by weight.

The weight average molecular weight of the biodegradable, water-insoluble polymer is preferably 2,000 to 100,000 daltons, more preferably 10,000 to 60,000 daltons, and even more preferably 25,000 to 50,000 daltons. Intrinsic viscosity thereof is preferably 0.1 to 0.9 dl/g, and more preferably 0.2 to 0.6 dl/g. When the intrinsic viscosity is too low, the polymer is degraded too fast and the physiologically active peptide may not be continuously released for the desired period. When the intrinsic viscosity is too high, the polymer degradation is too slow and thus the amount of released physiologically active peptide may be too small, and accordingly the pharmaceutical effect may not be exerted.

<Physiologically Active Peptide-Containing Microparticles>

The physiologically active peptide-containing microparticle according to the present invention contains the ionic complex of physiologically active peptide and water-soluble polymer and the biodegradable water-insoluble polymer.

The content of the ionic complex in the microparticle of the present invention is, with respect to the total weight of the microparticle (i.e., 100% by weight of the sum of the ionic complex and the biodegradable water-insoluble polymer), specifically 4% by weight to 40% by weight and more specifically 8% by weight to 20% by weight, and the content of the biodegradable water-insoluble polymer is specifically 60% by weight to 96% by weight and more specifically 80% by weight to 92% by weight.

The content of physiologically active peptide encapsulated in the microparticle is preferably 3 to 10% by weight, with respect to the total weight of microparticle, and encapsulation efficiency thereof is preferably 60 to 99% by weight, more preferably 70 to 99% by weight, and even more preferably 85 to 99% by weight, based on the amount of peptide used. The above encapsulation efficiency is equivalent to or higher than a level which is commonly obtained when a water-soluble active peptide is encapsulated in a biodegradable, water-insoluble polymer by a conventional microsphere preparation method. Furthermore, the present invention can resolve the conventional disadvantage when microparticles are prepared using active peptide alone, including the increased initial burst of drug due to the increased porosity and the failure in prolonging a continuous release period to the desired level due to the increased degradation rate of polymer.

The microparticle of the present invention may optionally contain a surfactant in order to uniformly disperse the ionic complex in the microparticle. As the surfactant, those commonly used in the art may be used without particular limitation. Specifically, examples of useful surfactants include polymer surfactants such as poloxamers, polyvinyl alcohol and polyoxyethylene sorbitan fatty acid esters, natural polymers such as gelatin and alkali salts of higher fatty acid. Such a surfactant may be present, for example, in an amount of 0.001 to 1% by weight with respect to 100 parts by weight of the microparticle.

The physiologically active peptide-containing microparticle according to the present invention may be prepared by mixing the ionic complex of physiologically active peptide and water-soluble polymer with the biodegradable, water-insoluble polymer in a non-aqueous solvent, followed by molding to micro-size and solvent removal.

Accordingly, in accordance with another aspect of the present invention, a method for preparing physiologically active peptide-containing microparticle comprising: a) homogeneously mixing an ionic complex of a physiologically active peptide and a water-soluble polymer with a biodegradable, water-insoluble polymer in a non-aqueous solvent; and b) removing the non-aqueous solvent from the resulting solution obtained in step a) to obtain microparticle.

The non-aqueous solvent that can be used for the preparation method of the microparticle according to the present invention is not particularly limited. Examples thereof include organic solvents such as methylene chloride, ethyl acetate, chloroform, acetone, N-methyl-2-pyrrolidone, N,N-dimethylformamide, tetrahydrofuran, dimethyl sulfoxide, hexafluoroisopropanol and mixtures thereof.

The amount of the biodegradable, water-insoluble polymer dissolved in the non-aqueous solvent is, for example, 5% by weight to 50% by weight and more specifically 10% by weight to 30% by weight. When the concentration is too low, an excessive amount of organic solvent is used and removal of the organic solvent is thus difficult. On the other hand, when the concentration of the biodegradable, water-insoluble polymer is too high, handling is difficult during the process and microwells may not be readily filled with the solution during subsequent microfabrication.

In step a), sonication may be performed to obtain a homogeneous dispersion (or solution), if necessary.

In one embodiment, the removal of the solvent to obtain microparticles in step b) can be carried out by a known microfabrication method (Acharya et. Al., J. Controlled Release, Vol. 141, Issue 3, Pages 314 to 319, Korean Patent Laid-open Publication No. 10-2010-7009002).

According to the microfabrication, step b) comprises:

b-1) filling a plurality of microwells placed in a water-soluble microtemplate with the solution obtained in step (a);

b-2) removing the non-aqueous solvent from the solution filled in the microwells to solidify the biodegradable, water-insoluble polymer; and b-3) collecting microparticles from the microtemplate.

The water-soluble microtemplate may be prepared by a known method. For example, an aqueous solution of water-soluble polymer such as gelatin, polyvinyl alcohol, agarose, poly(N-isopropyl acrylamide) and alginate is prepared (concentration may be about 1 to 80% by weight, varying according to the type of polymer), and the prepared aqueous hydrophilic polymer solution is applied to a silicone wafer provided with microstructures (that is, microwells) and solidified to give a microtemplate provided with a plurality of microwells. The microwells in microtemplate prepared as such are three-dimensional structures which have a diameter of about 1 to about 200 μm and a height of about 1 to about 200 μm. More specifically, the diameter may be about 20 to 100 μm and the height may be about 20 to 100 μm. Even more specifically, the diameter may be about 30 to 50 μm and the height may be about 30 to 50 μm.

In case of a gelatin aqueous solution, an aqueous solution containing 20 to 40% by weight of gelatin may be used, and in case of a polyvinyl alcohol solution, 5 to 10% by weight of an aqueous solution or a solution of a mixed solvent of ethanol/water may be used.

In step b-1), the resulting solution (or dispersion) obtained in step a) is applied to the microtemplate prepared as above (for example, a rectangle with a width of 4 cm and a length of 6 cm) to fill the microwells of templates with the solution.

In step b-2), the non-aqueous solvent is removed from the solution to solidify the biodegradable, water-insoluble polymer. The microtemplate filled with the solution may be kept at room temperature to allow the non-aqueous solvent to volatilize. Alternatively, the microtemplate filled with the solution may be kept under reduced pressure to remove the non-aqueous solvent. Solidification of the solution may be carried out at a room temperature or at a lower temperature.

In step b-3), the microtemplate having microwells filled with the solidified substance is added to an aqueous medium (for example, water) to dissolve the water-soluble microtemplate and thereby collect the microparticles.

If such a microfabrication is used, microparticles with a uniform size can be obtained and the possibility of remaining excessive organic solvent is eliminated. In addition, the necessity of using excessive water to collect the microparticles is eliminated and thus it is possible to prevent a large amount of waste water from being generated.

In another embodiment, the removal of the solvent to obtain microparticles in step b) may be carried out by a known emulsion evaporation method.

According to the emulsion evaporation, step b) comprises: b-i) adding the resulting solution obtained in step a) dropwise to an aqueous solution of the water-soluble polymer in the presence of a surfactant with stirring to remove the non-aqueous solvent and obtain microparticle.

As the aqueous solution of the water-soluble polymer, for example, an aqueous solution of water-soluble polymer such as gelatin, polyvinyl alcohol, agarose, poly(N-isopropyl acrylamide) or alginate may be used (concentration may be about 0.1 to 10% by weight, varying according to the type of polymer), and an aqueous solution of 0.1 to 5% by weight of polyvinyl alcohol is preferred.

The surfactant may be contained in the resulting solution obtained in step a), or in the aqueous solution of water-soluble polymer.

In such emulsion evaporation, when a polymer in an organic solvent is dispersed in an aqueous phase, the organic solvent is removed by extraction or evaporation and thus the polymer solubility decreases and the polymer is solidified. As a result, microparticles are formed.

The method for preparing microparticles of the present invention may further comprise a step of washing the obtained microparticles after step b). This subsequent washing step is carried out by using water or the like. As a result of the subsequent washing, any impurities present in the obtained microparticles and excessive peptides present on the surface thereof can be removed.

In addition, the method may further comprise a step of drying the microparticles by freeze-drying, vacuum drying or the like, after the washing. Through such drying, possibly remaining moisture and organic solvent can be removed further.

<Pharmaceutical Composition of Peptide Drug>

The microparticle of the present invention as explained above can continuously release the physiologically active peptide for a predetermined period, for example, preferably for at least several days to several weeks or several months after administration. The microparticle of the present invention may be dispersed, delivered or applied to the target site of the subject through a delivery route such as injection and/or subcutaneous, intramuscular, intraabdominal or dermal implant, and intramucosal administration. For example, the microparticle of the present invention may be administered in the form of a homogeneous suspension in a dispersion media such as an injection solution.

Accordingly, in accordance with another aspect of the present invention, provided is a pharmaceutical composition comprising the microparticle containing physiologically active peptide according to the present invention, and a pharmaceutically acceptable carrier.

For the pharmaceutical composition of the present invention, a pharmaceutically acceptable carrier suitably selected from commonly known pharmaceutically acceptable carriers may be used, depending on the intended formulation. The pharmaceutically acceptable carrier may comprise distilled water for injection, a thickener, an isotonic agent or a surfactant, and may contain a buffer if needed. For example, the pharmaceutically acceptable carrier is prepared by adding 3 to 5% of carboxymethylcellulose sodium, 0.9% (w/v) of sodium chloride, 0.1% to 0.5% of polysorbate 20 and the like to distilled water for injection. The viscosity of the prepared carrier may be 20 to 100 cP at room temperature.

As explained above, for the physiologically active peptide contained in the pharmaceutical composition of the present invention, any water-soluble physiologically active peptide known as a drug and a pharmaceutically acceptable salt thereof may be used without particular limitation, and specific examples thereof are described above. Accordingly, the type of diseases that can be effectively treated and/or prevented by the pharmaceutical composition of the present invention depends on the physiologically active peptide used. For example, when the pharmaceutical composition contains an LHRH agonist among LHRH analogs as the physiologically active peptide, the present pharmaceutical composition suppresses secretion of sexual hormones such as testosterone and estrogen, and thus can exhibit therapeutic and/or preventive effects on prostate cancer, breast cancer, endometriosis and the like which progress on the basis of hormone reactivity.

Hereinafter, the present invention will be described in more detail with reference to the following Examples. However, the examples are provided to illustrate the present invention only and should not be construed as limiting the protection scope of the present invention.

Examples 1 to 11: Preparation of Microparticles According to Microfabrication Method (1) Preparation of Dispersion or Solution of Ionic Complex of Goserelin Acetate and Polylactic Acid or a Derivative Thereof, and poly(lactide-co-glycolide) (PLGA)

According to Table 1, goserelin acetate was dissolved in distilled water at a concentration of 10 mg/mL and sodium polylactate (number average molecular weight of 1,500 Da) was dissolved in distilled water at concentrations of 20, 30 and 40 mg/mL. The sodium polylactate was prepared by a known method disclosed in Korean Patent Application No. 2002-63955. 3 ml of the respective aqueous solutions were mixed with each other such that the total volume was adjusted to 6 ml. The mixture was freeze-dried for 24 hours. As a biodegradable water-insoluble polymer, poly(lactide-co-glycolide) (PLGA) 7525DLG 4E (manufactured by Lakeshore Biomaterials) was added to a glass vial in an amount set forth in the following Table 1, and methylene chloride was added thereto, followed by dissolving 7525DLG 4E such that its concentration was adjusted to 20% by weight. The freeze-dried product was added thereto, followed by mixing to completely dissolve or homogeneously disperse it.

TABLE 1

| Examples | Goserelin acetate (mg) | Sodium polylactate (1,500 Da) (mg) | 7525 DLG 4E (mg) | Initial amount of goserelin added (%) |
|---|---|---|---|---|
| Ex. 1 | 30 | 60 | 1400 | 2.0 |
| Ex. 2 | 30 | 60 | 650 | 4.1 |
| Ex. 3 | 30 | 60 | 410 | 6.0 |
| Ex. 4 | 30 | 60 | 210 | 10.0 |
| Ex. 5 | 30 | 90 | 1400 | 2.0 |
| Ex. 6 | 30 | 90 | 650 | 3.9 |
| Ex. 7 | 30 | 90 | 380 | 6.0 |
| Ex. 8 | 30 | 90 | 180 | 10.0 |
| Ex. 9 | 30 | 120 | 1400 | 1.9 |
| Ex. 10 | 30 | 120 | 650 | 3.8 |
| Ex. 11 | 30 | 120 | 350 | 6.0 |

(2) Production of Water-Soluble Microtemplate 900 g of tepid distilled water was added to a 1 L vessel and 100 g of polyvinyl alcohol was slowly added thereto, while stirring. The solution was stirred with maintaining 40 to 50° C. to completely dissolve the polyvinyl alcohol and thereby prepare an aqueous solution of 10% polyvinyl alcohol. 100 g of the aqueous solution of polyvinyl alcohol was mixed with 100 g of ethanol and the mixture was allowed to be kept at 40 to 50° C. for 2 to 3 hours to prepare a 5% homogeneous PVA solution.

4 ml of the 5% PVA solution prepared above was added to a silicon wafer (diameter: 7 cm) having three-dimensional microstructures (microwells). After leveling the surface of the wafer, drying was conducted in an oven at 60° C. for 30 minutes. The dried PVA was separated from the silicon wafer to produce a microtemplate. The microtemplate had a disk shape with a diameter of 7 cm and the microwells had a diameter of 50 and a height of 50 μm.

(3) Application of Peptide-Containing Solution to Microtemplate

The microtemplate was fixed on a glass plate, 150/L of the solution of goserelin acetate-containing ionic complex and biodegradable, water-insoluble polymer prepared in step (1) was applied to the microtemplate repeatedly 5 to 10 times in a manner of straight line.

(4) Removal of Solvent and Collection of Microparticles

The microtemplate obtained in step (3) was kept at room temperature for 4 to 5 hours to allow methylene chloride to volatilize. Then, the microtemplate was added to 50 ml of tepid distilled water (35 to 45° C.) and shaken for 30 minutes to dissolve polyvinyl alcohol which constituted the water-soluble template, and then microparticles were separated according to the particle size by using 100 μm and 30 μm sieves. The microparticles having a particle size between 30 μm and 100 μm were collected, placed in a centrifuge tube and washed with tepid distilled water 2 to 3 times. The microparticles were centrifuged and freeze-dried for 24 hours.

Example 12: Preparation of Microparticles by Emulsion Evaporation Method

According to Table 2, goserelin acetate was dissolved in distilled water at a concentration of 10 mg/mL, sodium polylactate (number average molecular weight: 1,500 Da) was dissolved in distilled water at a concentration of 30 mg/mL. The respective aqueous solutions were mixed with each other at a weight ratio of 1:1 such that the total volume was adjusted to 6 ml. Precipitate was formed and freeze-dried for 24 hours. As a biodegradable water-insoluble polymer, poly(lactide-co-glycolide) (PLGA) 7525DLG 4E (manufactured by Lakeshore Biomaterials) was added to a glass vial in an amount set forth in the following Table 2, and methylene chloride was added thereto, followed by dissolution such that the concentration of 7525DLG 4E was adjusted to 20% by weight. The goserelin acetate-containing freeze-dried product and 5.0 mg of a surfactant (Tween 80) were added thereto, and dissolved or dispersed by vigorous stirring to obtain a homogeneous liquid. The homogeneous liquid was added dropwise to 500 mL of a 0.5% aqueous polyvinyl alcohol solution at room temperature and, at the same time, vigorous stirring was carried out by using a mixer for 20 minutes. The stirring speed was decreased, the reaction temperature was elevated to 40° C. and the organic solvent added was removed for one hour. The resulting product was centrifuged to collect microparticles, and the microparticles were washed with 200 mL of tepid distilled water and centrifuged again to obtain final microparticles.

TABLE 2

| Goserelin acetate (mg) | PLA-Na (1,500 Da) (mg) | 7525 DLG 4E (mg) | Methylene chloride (mg) | Surfactant (mg) |
|---|---|---|---|---|
| 30 | 90 | 1,400 | 5,000 | 5 |

Comparative Examples 1 to 3: Preparation of Microparticles Using Goserelin Acetate and PLGA (Microfabrication)

(1) Preparation of Dispersion or Solution of Goserelin Acetate and PLGA

According to Table 3, 30 mg of goserelin acetate, and 1400, 710 and 330 mg of poly(lactide-co-glycolide) (PLGA) 7525DLG 4E (manufactured by Lakeshore Biomaterials) as a biodegradable polymer, were added to glass vials, and methylene chloride was added thereto, followed by dissolution such that the concentration of 7525DLG 4E was adjusted to 20% by weight.

(2) Application of Peptide-Containing Solution to Microtemplate and Collection of Microparticles The same microtemplate as those used for Example 1 to 11 were fixed on a glass plate and 150 µl of a solution of goserelin acetate and a biodegradable polymer prepared in step (1) was applied to the microtemplate in a manner of straight line. The application was repeated 5 to 10 times and kept at room temperature for 4 to 5 hours to allow methylene chloride to volatilize. Then, microparticles were collected in the same manner as in Example 1 to 11.

TABLE 3

| Comp. Ex. | Goserelin acetate (mg) | 7525 DLG 4E (mg) | Initial amount of goserelin added (%) |
|---|---|---|---|
| Comp. Ex. 1 | 30 | 1400 | 2.1 |
| Comp. Ex. 2 | 30 | 710 | 4.1 |
| Comp. Ex. 3 | 30 | 330 | 8.3 |

Comparative Example 4: Preparation of Microparticles Using Goserelin Acetate and PLGA (Emulsion Evaporation)

Goserelin acetate was dissolved in tepid distilled water at a concentration of 30 mg/0.3 mL to obtain an aqueous phase. 1,250 mg of poly(lactide-co-glycolide)(PLGA) 7525DLG 4E (manufactured by Lakeshore Biomaterials) as a biodegradable polymer, 5 mg of Tween 80 as a surfactant and 5 ml of methylene chloride were mixed with together and dissolved under vigorous stirring to obtain a clear solution. The solution was added to the aqueous phase in which goserelin acetate was dissolved, followed by vigorous stirring to prepare an emulsion. The emulsion was added dropwise to 500 mL of a 0.5% aqueous polyvinyl alcohol solution at room temperature and, at the same time, vigorous stirring was carried out for 20 minutes by using a mixer. The stirring speed was decreased, the reaction temperature was elevated to 40° C. and the organic solvent added was removed for one hour. The resulting product was centrifuged to collect microparticles, the microparticles were washed with 200 mL of tepid distilled water and centrifuged again to obtain final microparticles.

Test Example 1: Shape of Microparticles

Figure 2:
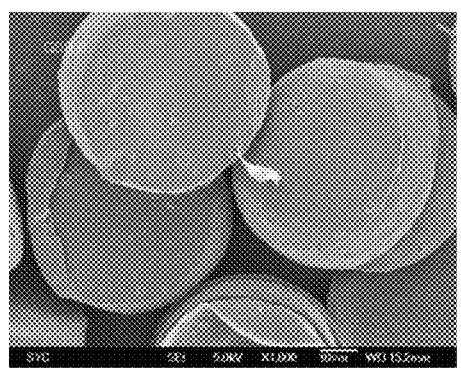
FIG. 2 is a scanning electronic microscope (SEM) image showing the microparticles prepared in Comparative Example 3 of the present invention.
Figure 3:
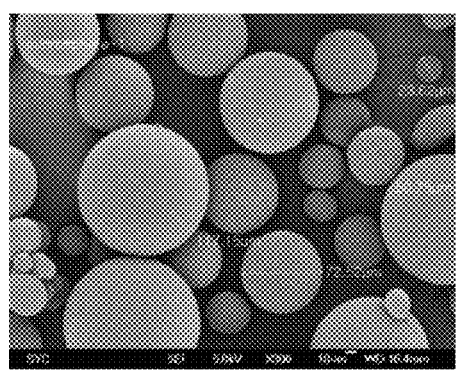
FIG. 3 is a scanning electronic microscope (SEM) image showing the microparticles prepared in Comparative Example 4 of the present invention.

In order to observe the surface of the prepared microparticles, about 10 mg of microparticles of Example 9, and Comparative Examples 3 and 4 were fixed to an aluminum stub, coated with platinum under vacuum of 0.1 torr at high voltage (10 Kv) for 3 minutes and mounted in a SEM, and the surface of the microparticles was observed using an image analysis program. The SEM images of microparticles are shown in FIGS. 1 to 3, respectively. It could be confirmed that the microparticles of Example 9 had more uniform and less porous surfaces, as compared with those of Comparative Example 3. In addition, it could be confirmed that microparticles of Comparative Example 4 had a considerably wide particle size distribution, as compared with those of Example 9.

Test Example 2: Encapsulation Ratio of Goserelin in Microparticles 2 ml of methylene chloride was added to about 10 mg of microparticles of Examples and Comparative Examples, followed by complete dissolution. 8 ml of a 0.1M acetate buffer (pH 4.0) was added to the solution, shaken for 10 minutes to transport goserelin to the aqueous solution layer and centrifuged to collect the aqueous solution layer. The aqueous solution layer was filtered through a 0.45 syringe filter, the content of goserelin was measured by HPLC and the results are shown in Table 4. The column used herein was a CAPCELL PAK C18 (inner diameter: 2.0 mm, length: 15 cm), UV detection was performed at a wavelength of 230 nm, injected amount was 20 μl and the flow rate of mobile phase was 0.2 mL/min. The mobile phases used were (a) water containing 0.1% TFA and (b) acetonitrile containing 0.1% TFA, and the solvent ratio was changed such that the solvent (b) became from 0% to 65% for 30 minutes.

TABLE 4

| Examples | Goserelin acetate:PLA-Na | Initial amount of goserelin added (%) | Amount of goserelin encapsulated (%) | Drug encapsulation ratio (%) |
|---|---|---|---|---|
| Ex. 1 | 1:2 | 2.0 | 0.9 | 45 |
| Ex. 2 | 1:2 | 4.1 | 1.6 | 39 |
| Ex. 3 | 1:2 | 6.0 | 2.1 | 35 |
| Ex. 4 | 1:2 | 10.0 | 4.8 | 48 |
| Ex. 5 | 1:3 | 2.0 | 1.6 | 80 |
| Ex. 6 | 1:3 | 3.9 | 3.3 | 85 |
| Ex. 7 | 1:3 | 6.0 | 3.0 | 50 |
| Ex. 8 | 1:3 | 10.0 | 4.1 | 41 |
| Ex. 9 | 1:4 | 1.9 | 1.6 | 84 |
| Ex. 10 | 1:4 | 3.8 | 2.6 | 68 |
| Ex. 11 | 1:4 | 6.0 | 3.2 | 53 |
| Ex. 12 | 1:3 | 2.0 | 1.7 | 85 |
| Comp. Ex. 1 | 1 | 2.1 | 0.5 | 24 |
| Comp. Ex. 2 | 1 | 4.1 | 0.8 | 20 |
| Comp. Ex. 3 | 1 | 8.3 | 1.0 | 12 |
| Comp. Ex. 4 | 1 | 2.3 | 1.0 | 33 |

As can be seen from Table 4 above, Comparative Examples 1 to 4 exhibited low encapsulation ratios, as compared with Examples of the present invention, and in Comparative Examples 1 to 3, the amount of goserelin encapsulated in microparticles with respect to the total weight of microparticles could not be increased to 1% or more, although the initially amount of goserelin acetate added increased.

Test Example 3: In Vitro Long-Period Release Test of Microparticles 50 mg of microparticles prepared in Examples 1, 2 and 9 and Comparative Example 3 were added to a test tube, 50 mL of a pH 7.4 phosphate buffer was added thereto, stored in a stirrer set at 37° C., the supernatant was collected after 6 hours, and 1, 3, 5, 7, 14, 21 and 28 days and the amount of released goserelin was measured by HPLC. The results are shown in FIG. 4.

Figure 4:
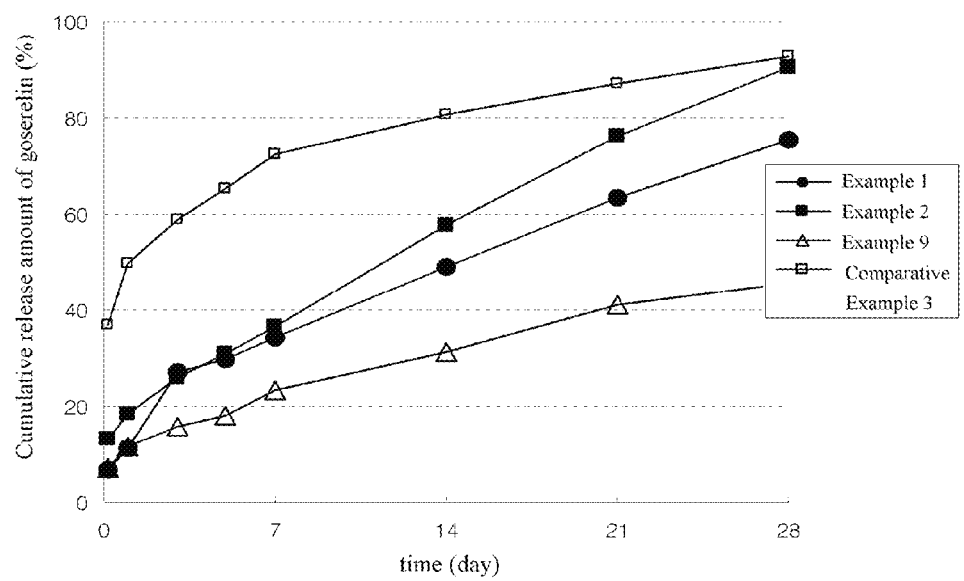
FIG. 4 is a graph showing the cumulative release amount of goserelin over time in Test Example 3 (in vitro long-period release test) of the present invention.

As can be seen from FIG. 4, microparticles of Examples according to the present invention exhibited decreased initial drug release amounts and superior long-term continuous release properties. Thus, it could be confirmed that they were remarkably advantageous as sustained formulations, as compared with Comparative Examples.

What is claimed is:

1. A method for preparing physiologically active peptide-containing microparticle comprising:
   1) mixing a physiologically active peptide with an ionic water-soluble polymer in an aqueous medium to form an ionic complex of the physiologically active peptide and the water-soluble polymer;
   2) drying the ionic complex of the physiologically active peptide and the water-soluble polymer obtained in step 1);
   3) homogeneously mixing the ionic complex of the physiologically active peptide and the water-soluble polymer obtained in step 2) with a biodegradable, water-insoluble polymer in a non-aqueous solvent; and
   4) removing the non-aqueous solvent from the resulting solution obtained in step 3) to obtain microparticles;
   wherein the water-soluble polymer has a number average molecular weight of 500 to 5,000 daltons, and is the compound represented by Formula 2 or 6 below:

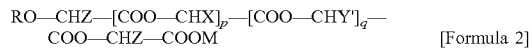
[Formula 2]

wherein X is methyl group; Y' is hydrogen atom or phenyl group; p is an integer of 0 to 25 and q is an integer of 0 to 25 provided that p+q is an integer of 5 to 25; R is hydrogen atom, or acetyl group, benzoyl group, decanoyl group, palmitoyl group, methyl group or ethyl group; M is H, Na, K, or Li; and Z is hydrogen atom, methyl group or phenyl group,

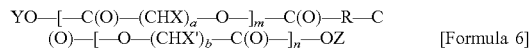
[Formula 6]

wherein each of X and X' is independently hydrogen, alkyl or aryl; each of Y and Z is independently H, Na, K, or Li; each of m and n is independently an integer of 0 to 95 provided that 5<m+n<100; each of a and b is each independently an integer of 1 to 6; and R is substituted or unsubstituted —$(CH_2)_k$— in which k is an integer of 0 to 10, divalent alkenyl having 2 to 10 carbon atoms, divalent aryl having 6 to 20 carbon atoms, or a combination thereof, wherein the biodegradable, water-insoluble polymer has a weight average molecular weight of 10,000 to 100,000 daltons, and is one or more selected from the group consisting of polylactide, polyglycolide, poly(lactide-co-glycolide), polyorthoester, polycaprolactone, polydioxanone polyalkylcarbonate, polyanhydride and copolymers thereof, and wherein the microparticle has a uniform particle size of between 30 μm and 100 μm, a drug encapsulation ratio of between 35% and 85%, and exhibits decreased initial drug release amounts of less than 20% and superior long-term continuous release properties of greater than 40% after 14 days.

2. The method according to claim 1, wherein the non-aqueous solvent is selected from the group consisting of methylene chloride, ethyl acetate, chloroform, acetone, N-methyl-2-pyrrolidone, N,N-dimethylformamide, tetrahydrofuran, dimethyl sulfoxide, hexafluoroisopropanol and mixtures thereof.

3. The method according to claim 1, wherein step 4) comprises:
   4-1) filling a plurality of microwells placed in a water-soluble microtemplate with the solution obtained in step 3);
   4-2) removing the non-aqueous solvent from the solution filled in the microwells to solidify the biodegradable, water-insoluble polymer; and
   4-3) collecting microparticles from the microtemplate.

4. The method according to claim 3, wherein the water-soluble microtemplate is produced from one or more water-soluble polymers selected from the group consisting of gelatin, polyvinyl alcohol, agarose, poly(N-isopropyl acrylamide), alginate and mixtures thereof.

5. The method according to claim 3, wherein, in step 4-3), the collection of microparticles is carried out by dissolving the microtemplate in an aqueous medium.

6. The method according to claim 1, wherein step 4) comprises:
   4-i) adding the resulting solution obtained in step 3) dropwise to an aqueous solution of the water-soluble polymer in the presence of a surfactant with stirring to remove the non-aqueous solvent and obtain microparticle.

7. The method according to claim 1, wherein the water-soluble polymer has a number average molecular weight of 500 to 3,000 daltons.

8. The method according to claim 1, wherein the physiologically active peptide is selected from the group consisting of luteinizing hormone-releasing hormone (LHRH) agonists, somatostatin and analogs thereof, glucagon-like peptides (GLP), parathyroid hormone and analogs thereof, insulin-like growth factors, epidermal growth factors, platelet-derived growth factors, fibroblast growth factors, transforming growth factors, growth hormone releasing factors, amylin analogs, peptide YY (PYY), protein synthesis-stimulating peptides, gastrin inhibitory peptides, vasoactive intestinal peptides, and pharmaceutically acceptable salts thereof.

9. The method according to claim 1, wherein the physiologically active peptide is present in an amount of 1.0 to 10% by weight with respect to the total weight of the microparticles.

10. The method according to claim 1, wherein the content of the ionic complex is 4% by weight to 40% by weight, based on the total weight of the microparticles.

11. The method according to claim 1, wherein the physiologically active peptide and the ionic water-soluble polymer are mixed with a mixing ratio of 1:1 to 10 as a molar ratio.

12. The method according to claim 1, wherein the water-soluble polymer is the compound represented by Formula 2.

13. The method according to claim 1, wherein the water-soluble polymer is PLA-COONa.

* * * * *